US006277787B1

(12) United States Patent
Malefyt et al.

(10) Patent No.: US 6,277,787 B1
(45) Date of Patent: Aug. 21, 2001

(54) SYNERGISTIC HERBICIDAL METHODS AND COMPOSITIONS

(75) Inventors: Timothy Malefyt, Yardley, PA (US); Robert M. Watkins, Starkville, MS (US); Frederick P. Salzman, Lawrenceville, NJ (US)

(73) Assignee: American Cyanamid Co., Madison, NJ (US)

( * ) Notice: Subject to any disclaimer, the term of this patent is extended or adjusted under 35 U.S.C. 154(b) by 0 days.

(21) Appl. No.: 09/395,716

(22) Filed: Sep. 14, 1999

Related U.S. Application Data

(60) Provisional application No. 60/100,128, filed on Sep. 14, 1998.

(51) Int. Cl.$^7$ ............................ A01N 43/50; A01N 57/02
(52) U.S. Cl. ..................... 504/128; 504/127; 504/128; 504/130
(58) Field of Search ................................ 504/127, 128, 504/130

(56) References Cited

U.S. PATENT DOCUMENTS

| | | | |
|---|---|---|---|
| 4,816,060 | 3/1989 | Steller et al. ............................ 71/92 |
| 5,206,021 | 4/1993 | Dookhith et al. ..................... 424/405 |
| 5,478,795 | 12/1995 | Watkins, Jr. ........................... 504/130 |
| 5,672,617 | 9/1997 | Wachtler et al. ..................... 514/407 |
| 6,127,317 | * 10/2000 | Castro et al. .......................... 504/128 |

FOREIGN PATENT DOCUMENTS

| | | | |
|---|---|---|---|
| 220 902 A2 | 5/1987 | (EP) ............................. A01N/57/20 |
| 256 414 A2 | 2/1988 | (EP) ............................. A01N/25/22 |
| 433 577 A1 | 6/1991 | (EP) ............................. A01N/25/04 |
| 2233229 | 1/1991 | (GB) ............................. A01N/57/20 |
| WO 96/08148 | 3/1996 | (WO) ............................ A01N/41/10 |

OTHER PUBLICATIONS

Rao A. S. (CA 131:224816, abstract of Weed Technol. (1999), 13(2), 361–366).*

Starke et al. (CA 130:193048, abstract of Weed Technology (1998), 46(6), 652–660), 1999.*

Bruff et al., "Tank–mix combinations for weed control in stale seedbed soybean (*Glycine max*)", Weed Technology, 6(1), pp. 45–51 (1992).

Lanie et al., "Herbicide Combinations for Soybean (*Glycine max*) Planted in Stale Seedbed", Weed Technology, 8(1), pp. 17–22 (1994).

CA124: 281878 abstract of Sanders et al., "Control of nut grass (*Cyperus rotundus*) in asparagus", Proc. N. Z. Plant Prot. Conf., 48$^{th}$, pp. 322–326 (1995).

\* cited by examiner

*Primary Examiner*—Sabiha Qazi
(74) *Attorney, Agent, or Firm*—John W. Hogan, Jr.; Barbara V. Maurer

(57) ABSTRACT

The present invention provides a method for the synergistic control of undesirable plants such as Ipomoea, Cyperus, Sida and Euphorbia which comprises applying to the plants or their locus a synergistically effective amount of a combination of glyphosate and an imidazolinone compound. Further provided are synergistic herbicidal compositions comprising glyphosate and an imidazolinone compound.

16 Claims, No Drawings

SYNERGISTIC HERBICIDAL METHODS AND COMPOSITIONS

This application claims benefit of U.S. patent application Ser. No. 60/100,128 filed on Sep. 14, 1998.

BACKGROUND OF THE INVENTION

Certain weeds such as Ipomoea, Cyperus, Sida and Euphorbia are particularly difficult to control. Their full-season competition can reduce crop yields and cause significant economic loss in row-crop production. One of the most common practices for controlling these troublesome weeds is the postemergent application of a herbicide. However, there is no single selective herbicide currently available which will give economic control of these weeds.

Glyphosate [(N-phosphonomethyl)glycine] is a highly effective herbicide with a broad spectrum of activity. However, certain agronomically important weed species require relatively high application rates of glyphosate for effective control. High rates of glyphosate can lead to undesirable increased selection pressure. Glyphosate tolerance, particularly in Ipomoea, is a recognized problem in the field. Therefore, new weed control methods and compositions which effectively lower glyphosate application rates while providing broad spectrum weed control are highly desirable.

SUMMARY OF THE INVENTION

Surprisingly, it has now been found that the combination of glyphosate with an imidazolinone compound provides synergistic weed control. Advantageously, the synergistic combination of the invention allows for lower application rates of glyphosate with concomittant increased spectrum of weed control. Moreover, the synergistic herbicidal methods and compositions of the invention allow for effective resistance management programs and provide improved control of pestiferous weeds such as Ipomoea in glyphosate-resistant crop production.

The present invention provides a method for the synergistic control of undesirable plants such as Ipomoea, Cyperus, Sida or Euphorbia which comprises applying to the locus of said plants or to the foliage or stems of said plants a synergistically effective amount of a combination of glyphosate and at least one imidazolinone compound selected from the group consisting of imazethapyr, the R isomer thereof or a salt thereof; imazaquin, the R isomer thereof or a salt thereof; imazapic, the R isomer thereof or a salt thereof; imazamox, the R isomer thereof or a salt thereof; imazapyr, the R isomer thereof or a salt thereof; and mixtures thereof.

The present invention also provides a synergistic herbicidal composition which comprises an agriculturally acceptable carrier and a synergistically effective amount of a combination of glyphosate and at least one imidazolinone compound selected from the group consisting of imazethapyr, the R isomer thereof or a salt thereof; imazaquin, the R isomer thereof or a salt thereof; imazapic, the R isomer thereof or a salt thereof; imazamox, the R isomer thereof or a salt thereof; imazapyr, the R isomer thereof or a salt thereof; and mixtures thereof.

DETAILED DESCRIPTION OF THE INVENTION

Glyphosate [(N-phosphonomethyl)glycine] is a highly effective broad spectrum herbicide. However, certain troublesome weeds such as Ipomoea, Sida, Cyperus and Euphorbia may require very high application rates of glyphosate for effective control. High application rates of glyphosate may decrease the margin of crop safety, increase the potential development of weed tolerance and result in the loss of economic weed control.

Surprisingly, it has now been found that the application of a combination of glyphosate plus at least one imidazolinone compound selected from imazethapyr, the R isomer thereof or a salt thereof; imazaquin, the R isomer thereof or a salt thereof; imazamox, the R isomer thereof or a salt thereof; imazapic, the R isomer thereof or a salt thereof; and imazapyr, the R isomer thereof or a salt thereof provides synergistic control of troublesome weeds, particularly Ipomoea, Sida, Cyperus and Euphorbia, especially Ipomoea. That is, the application of the combination of the invention gives a mutual reinforcing action such that the application rates of the individual herbicidal components can be reduced and still the same herbicidal effect is achieved or, alternatively, the application of the combination of herbicidal components demonstrates a greater herbicidal effect than expected from the effect of the application of the individual herbicidal components when applied singly at the rate at which they are present in the combination (synergistic effect).

As used in the specification and claims, the term glyphosate designates the compound N-(phosphonomethyl)-glycine or the agriculturally acceptable salts thereof. Similarly, the terms used for the imidazolinone compounds imazethapyr, imazaquin, imazapic, imazamox and imazapyr as they appear in the specification and claims designate the compound, the R isomer thereof, or the agriculturally acceptable salt thereof. The imidazolinone compounds and their corresponding chemical names are listed herein below.

Imazethapyr designates 5-ethyl-2-(4-isopropyl-4-methyl-5-oxo-2-imidazolin-2-yl) nicotinic acid, the R isomer thereof, a salt thereof, or mixtures thereof.

Imazaquin designates 2-(4-isopropyl-4-methyl-5-oxo-2-imidazolin-2-yl) quinolinecarboxylic acid, the R isomer thereof, a salt thereof, or mixtures thereof.

Imazapic designates 2-(4-isopropyl-4-methyl-5-oxo-2-imidazolin-2-yl)-5-methylnicotinic acid, the R isomer thereof, a salt thereof, or mixtures thereof.

Imazamox designates 2-(4-isopropyl-4-methyl-5-oxo-2-imidazolin-2-yl)-5-(methoxymethyl)nicotinic acid, the R isomer thereof, a salt thereof, or mixtures thereof.

Imazapyr designates 2-(4-isopropyl-4-methyl-5-oxo-2-imidazolin-2-yl)nicotinic acid, the R isomer thereof, a salt thereof, or mixtures thereof.

In the context of the present invention, the term agriculturally acceptable salt includes alkali metal, ammonium, alkyl sulphonium or alkylphosphonium salt or the quatenary salt of an amine having a molecular weight of less than 300. In particular, the term includes isopropylammonium, ammonium, sodium and trimesium, especially isopropylammonium and ammonium.

As used in the specification and claims, the term R isomer designates the optical isomer of an imidazolinone compound having the R configuration assigned to the assymetric carbon in the imidazolinone ring which is substituted by a methyl and an isopropyl group, for example the R isomer of the imidazolinone compound imazapyr is shown low.

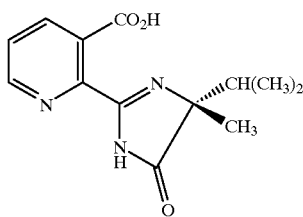

In general, commercial formulations of glyphosate are aqueous solutions of an agriculturally acceptable salt such as glyphosate-isopropylammonium, glyphosate-sesquisodium, glyphosate trimesium and the like. Similarly, imidazolinone herbicides and their agriculturally acceptable salts are commercially available as aqueous solutions. Additionally, imidazolinone herbicides are commercially available as dispersible granules, soluble granules and the like. In actual practice, the combination of the invention may be applied simultaneously (as a tank mix or a premix), separately or sequentially.

Thus, in accordance with the method of invention a synergistically effective amount of a combination of glyphosate and an imidazolinone compound selected from the group consisting of imazethapyr, imazaquin, imazapic, imazamox and imazapyr is applied to the locus, foliage or stems of undesirable plants, particularly plants selected from the genera Ipomoea, Cyperus, Sida and Euphorbia, preferably *Ipomoea lacunosa, Cyperus rotundus, Sida spinosa* and *Euphorbia maculata*, more preferably *Ipomoea lacumosa*.

Preferred combinations of the invention are those combinations wherein the weight/weight (wt/wt) ratio of glyphosate:imidazolinone compound is about 3:1 to 65:1. More preferred combinations of the invention are combinations of glyphosate and imazethapyr wherein the wt/wt ratio of glyphosate:imazethapyr is about 8:1 to 12:1 or combinations of glyphosate and imazaquin wherein the wt/wt ratio of glyphosate:imazaquin is about 3:1 to 10:1 or combinations of glyphosate and imazapic wherein the wt/wt ratio of glyphosate:imazapic is about 15:1 to 65:1 or combinations of glyphosate and imazamox wherein the wt/wt ratio of glyphosate:imazamox is about 20:1 to 65:1.

The synergistically effective amount of the combination of glyphosate and an imidazolinone compound selected from imazethapyr, imazaquin, imazapic, imazamox and imazapyr may vary according to prevailing conditions such as the particular imidazolinone compound present, weed pressure, application timing, weather conditions, soil conditions, mode of application, topographical character, target crop 20 species and the like. In general, a synergistic effect may be achieved at application rates of about 200 g/ha–800 g/ha of glyphosate in combination with about 8.0 g/ha–150 g/ha of an imidazolinone compound, preferably about 480 g/ha–720 g/ha of glyphosate in combination with about 60 g/ha–80 g/ha of imazethapyr.

The present invention also provides a synergistic herbicidal composition comprising an agriculturally acceptable carrier and a synergistically effective amount of a combination of glyphosate and an imidazolinone compound selected from imazethapyr, imazaquin, imazapic, imazamox and imazapyr, preferably imazethapyr. The agriculturally acceptable carrier may be a solid or a liquid, preferably a liquid, more preferably water. While not required, the combination composition of the invention may also contain other additives such as fertilizers, inert formulation aids, i.e. surfactants, emulsifiers, defoamers, dyes, extenders and the like.

Compositions according to the invention may be formulated in any conventional form, for example in the form of a twin pack, or as an aqueous concentrate, soluble granular, dispersible granular and the like.

Preferred compositions of the invention are those compositions wherein the glphosate and imidazolinone compound are present in a wt/wt ratio of about 3:1 to 65:1 glyphosate:imidazolinone compound. More preferred inventive compositions are those compositions wherein the imidazolinone compound is imazethapyr and the wt/wt ratio is about 8:1 to 12:1 glyphosate:imazethapyr.

In actual practice, a tank mix of a commercially convenient association or presentation of glyphosate and an imidazolinone compound selected from imazethapyr, imazaquin, imazapic, imazamox and imazapyr may be applied to the foliage of the crop, or the glyphosate and said imidazolinone compound may be applied separately or sequentially, or the combination compositions of the invention may be applied in a single combined form as described hereinabove.

The synergistically effective amount of a combination of glyphosate and an imidazolinone compound suitable for use in the composition of the invention is that amount sufficient to provide about 200 g/ha–1200 g/ha of glyphosate and about 8.0 g/ha–150 g/ha of an imidazolinone compound, preferably about 400 g/ha–800 g/ha of glyphosate and about 55 g/ha–100 g/ha of imazethapyr, more preferably about 480 g/ha–720 g/ha of glyphosate and about 60 g/ha to 80 g/ha of imazethapyr.

The synergistic herbicidal compositions of the invention provide effective resistance management programs in crop production, for example glyphosate-resistant soybean, canola, sugarbeet, corn, wheat, rice and the like crop production, preferably glyphosate-resistant soybean crop production.

For a more clear understanding of the invention, specific examples thereof are set forth below. These examples are merely illustrative, and are not to be understood as limiting the scope and underlying principles of the invention in any way.

In the following examples, synergism is determined by the Colby[1] method, i.e. the expected (or predicted) response of the combination is calculated by taking the product of the observed response for each individual component of the combination when applied alone divided by 100 and subtracting this value from the sum of the observed response for each component when applied alone. Synergism of the combination is then determined by comparing the observed response of the combination to the expected (or predicted) response as calculated from the observed responses of each individual component alone. If the observed response of the combination is significantly greater than the expected (or predicted) response as determined by Fisher's protected Least Significant Difference (LSD) test using significance level 0.05, than the combination is said to be synergistic and falls within the definition of synergistic effect as previously defined. [1]Colby, S. R., Weeds, 1967 (15), p. 20–22

The foregoing is illustrated mathematically below, wherein a combination, C, is composed of component A plus component B and Obs. designates the observed response of the combination C.

$$(A + B) - \frac{AB}{100} = \text{Expected response (Exp.)}$$

$$\text{Synergism} \equiv (\text{Obs.} - \text{Exp.}) > LSD$$

EXAMPLE 1

Evaluation Of The Herbicidal Activity Of A Combination Of lyphosate Ana Imazethapyr In this evaluation, pitted morningglory plants (*Ipomoea lacunosa*) are grown in standard greenhouse soil until they have reached the 6-leaf stage. Said plants are then sprayed with an aqueous solution of the test compound using a spray nozzle operating at 30 psi for a predetermined time so as to obtain a range of application rates of about 20 g/ha to 720 g/ha. Each treatment is replicated 3 times. After spraying, the plants are placed on greenhouse benches and are cared for in a manner commensurate with standard greenhouse practice. At 4 weeks after treatment, the plants are examined, and the % weed control as compared to the untreated check is recorded. Also at 4 weeks after treatment, the plant height is measured and recorded as % height reduction as compared to the height of the untreated check. Plant heights are measured by stretching out the vines and measuring from the soil surface to the tip of the vine.

The data obtained are analyzed using conventional statistical analysis techniques to determine the least significant difference (LSD) or standard deviation. The Colby method of analysis is used to determine the resultant biological effect of the combination treatment as compared to the biological effect of each component of the combination when applied alone.

| TEST COMPOUNDS | SOURCE |
|---|---|
| Glyphosate, isopropylammonium salt 4AS | ROUNDUP ®[1] |
| Imazethapyr 100AS | PIVOT ® H[2] |

[1]manufactured by Monsanto
[2]manufactured by American Cyanamid Co.

TABLE I

Evaluation of Weed Control

| Glyphosate | Imazethapyr | Weed Control | | |
|---|---|---|---|---|
| g/ha | g/ha | Observed | Expected | (Obs.-Exp.)[1] |
| 0 | 0 | 0.00 | — | |
| 0 | 60 | 3.33 | — | |
| 0 | 80 | 0.00 | — | |
| 0 | 100 | 30.00 | — | |
| 480 | 0 | 3.33 | — | |
| 720 | 0 | 23.33 | — | |
| 480 | 60 | 82.67 | 6.67 | 76.00* |
| 480 | 80 | 86.00 | 3.33 | 82.67* |
| 480 | 100 | 84.33 | 42.00 | 42.33* |
| 720 | 60 | 85.00 | 26.00 | 59.00* |
| 720 | 80 | 86.67 | 23.33 | 63.33* |
| 720 | 100 | 88.33 | 54.00 | 34.33* |

[1]LSD (0.05) = 17.4
*Synergistic, i.e. (obs.-exp.) > LSD

As can be seen from the data shown in Table I, application of a combination of glyphosate plus imazethapyr gave significantly greater weed control than that which could be predicted from the weed control resulting from the application of either imazethapyr alone or glyphosate alone.

TABLE II

Evaluation of Plant Height Reduction

| Gly-phosate | Imazethapyr | Height | Height Reduction | | |
|---|---|---|---|---|---|
| g/ha | g/ha | (cm) | Observed | Expected | (Obs.-Exp.)[1] |
| 0 | 0 | 169 | 0.00 | — | |
| 0 | 60 | 143 | 15.35 | — | |
| 0 | 80 | 143 | 15.37 | — | |
| 0 | 100 | 115 | 31.47 | — | |
| 480 | 0 | 141 | 16.75 | — | |
| 720 | 0 | 106 | 37.11 | — | |
| 480 | 60 | 61 | 63.49 | 29.75 | 33.74* |
| 480 | 80 | 60 | 64.58 | 29.58 | 35.00* |
| 480 | 100 | 59 | 64.87 | 43.71 | 21.16* |
| 720 | 60 | 62 | 63.55 | 46.40 | 17.15 |
| 720 | 80 | 53 | 68.70 | 46.64 | 22.06* |
| 720 | 100 | 52 | 68.94 | 55.81 | 13.14 |

[1]LSD (0.05) = 17.4
*Synergistic, i.e. (obs.-exp.) > LSD

As can be seen from the data shown in Table II application of a combination of glyphosate plus imazethapyr at 4 of the 6 rates tested gave significantly greater height reduction than that which could be predicted from the application of either glyphosate alone or imazethapyr alone.

EXAMPLE 2

Evaluation Of The Herbicidal Actvity Of A Combination Of Glyphosate And Imazapic In this evaluation pitted morningglory plants (*Ipomoea lacunosa*) are grown in a 1:1 mixture of sandy loam soil and masonry sand until they have reached the 5-leaf stage. Said plants are then sprayed with an aqueous solution of test cmpound using a $Co_2$-pressurized spray chamber. Each treatment is replicated 4 times. After spraying, the plants are placed on greenhouse benches and cared for in a manner commensurate with conventional greenhouse practice. At 4 weeks after treatment the plants are visually examined and % weed control as compared to the untreated check is recorded. Also at 4 weeks after treatment, the number of leaves are counted and are recorded as % leaf reduction as compared to the untreated check. After the visual ratings, the plant is excised at the soil surface and the excised vegetation is weighed and measured. Plant fresh weight and height are recorded as % weight reduction as compared to untreated check and as % height reduction as compared to untreated check.

The data are analyzed using standard statistical analysis techniques to determine the least significant difference (LSD) or standard deviation. The Colby method is used to determine if the test combination demonstrates a synergistic interaction.

| TEST COMPOUNDS | SOURCE |
|---|---|
| Glyphosate, isopropylammonium salt | ROUNDUP ® ULTRA[1] |
| Imazapic | CADRE ®[2] |

[1]manufactured by Monsanto
[2]manufactured by American Cyanamid Co.

TABLE III

Evaluation of Weed Control

| Glyphosate | Imazapic | % Weed Control | | |
|---|---|---|---|---|
| g/ha | g/ha | Observed | Expected | (Obs.-Exp.)[1] |
| 0 | 0 | 0 | — | |
| 0 | 8.97 | 35.00 | — | |
| 0 | 13.45 | 28.75 | — | |
| 0 | 17.93 | 20.00 | — | |
| 280.2 | 0 | 23.75 | — | |
| 560.4 | 0 | 5.00 | — | |
| 280.2 | 8.97 | 51.25 | 50.38 | 0.88 |
| 280.2 | 13.45 | 73.75 | 45.81 | 27.94* |
| 280.2 | 17.93 | 77.50 | 39.00 | 38.50* |
| 560.4 | 8.97 | 55.00 | 38.25 | 16.75* |
| 560.4 | 13.45 | 78.75 | 32.31 | 46.44* |
| 560.4 | 17.93 | 86.25 | 24.00 | 62.25* |

[1]LSD (0.05) = 10.76
*Synergistic, i.e. (obs.-exp.) > LSD

TABLE IV

Evaluation of Leaf Reduction

| Gly-phosate | Imazapic | Number | % Leaf Reduction | | |
|---|---|---|---|---|---|
| g/ha | g/ha | of leaves | Observed | Expected | (Obs.-Exp.)[1] |
| 0 | 0 | 13.3 | 0 | — | |
| 0 | 8.97 | 8.8 | 26.34 | — | |
| 0 | 13.45 | 9.0 | 32.46 | — | |
| 0 | 17.93 | 6.0 | 50.89 | — | |
| 280.2 | 0 | 10.8 | 6.66 | — | |
| 560.4 | 0 | 12.5 | 0.17 | — | |
| 280.2 | 8.97 | 5.3 | 58.80 | 16.24 | 42.56* |
| 280.2 | 13.45 | 3.8 | 69.44 | 36.62 | 32.81* |
| 280.2 | 17.93 | 5.5 | 55.23 | 46.61 | 8.62 |
| 560.4 | 8.97 | 5.5 | 54.48 | 19.71 | 34.77* |
| 560.4 | 13.45 | 4.5 | 65.52 | 32.22 | 33.30* |
| 560.4 | 17.93 | 3.0 | 77.29 | 47.34 | 29.96* |

[1]LSD (0.05) = 23.28
*Synergistic, i.e. (obs.-exp.) > LSD

EXAMPLE 3

Evaluation Of The Herbicidal Activity Of A Combination Of Glyphosate And Imazamox Using essentially the same procedure described in Example 2 hereinabove, 5-leaf pitted morningglory plants are treated with test compounds and evaluated at 3 weeks after treatment. Each treatment is replicated 4 times. The data are averaged and shown in Tables V and VI below.

| TEST COMPOUND | SOURCE |
|---|---|
| Glyphosate, isopropylammonium salt | ROUNDUP ® ULTRA[1] |
| Imazamox | RAPTOR ®[2] |

[1]manufactured by Monsanto
[2]manufactured by American Cyanamid Co.

TABLE V

Evaluation of Weed Control

| Glyphosate | Imazamox | % Weed Control | | |
|---|---|---|---|---|
| g/ha | g/ha | Observed | Expected | (Obs.-Exp.)[1] |
| 0 | 0 | 0 | — | |
| 0 | 8.97 | 5.00 | — | |
| 0 | 17.93 | 32.50 | — | |
| 0 | 26.90 | 66.25 | — | |
| 560.4 | 0 | 7.50 | — | |
| 560.4 | 8.97 | 45.00 | 12.13 | 32.88* |
| 560.4 | 17.93 | 78.75 | 37.63 | 41.13* |
| 560.4 | 26.90 | 78.75 | 68.81 | 9.94 |

[1]LSD (0.05) = 15.55
*Synergistic, i.e. (obs.-exp.) > LSD

TABLE VI

Evaluation of Fresh Weight Reduction

| Glyphosate | Imazanox | Weight | % Weight Reduction | | |
|---|---|---|---|---|---|
| g/ha | g/ha | (g) | Observed | Expected | (Obs.-Exp.)[1] |
| 0 | 0 | 4.38 | 0 | — | |
| 0 | 8.97 | 4.19 | 4.19 | — | |
| 0 | 17.93 | 4.49 | -4.55 | — | |
| 0 | 26.90 | 3.02 | 30.41 | — | |
| 560.4 | 0 | 5.22 | -22.39 | — | |
| 560.4 | 8.97 | 3.61 | 14.02 | -17.06 | 31.08 |
| 560.4 | 17.93 | 2.82 | 32.80 | -31.26 | 64.06* |
| 560.4 | 26.90 | 2.30 | 47.16 | -13.86 | 33.30 |

[1]LSD (0.05) = 35.34
*Synergistic, i.e. (obs.-exp.) > LSD

TABLE VII

Evaluation of Leaf Reduction

| Gly-phosate | Imazanox | Number | % Leaf Reduction | | |
|---|---|---|---|---|---|
| g/ha | g/ha | of Leaves | Observed | Expected | (Obs.-Exp.)[1] |
| 0 | 0 | 21.75 | 0 | — | |
| 0 | 8.97 | 17.50 | 15.00 | — | |
| 0 | 17.93 | 11.00 | 47.98 | — | |
| 0 | 26.90 | 7.00 | 66.21 | — | |
| 560.4 | 0 | 23.00 | -16.18 | — | |
| 560.4 | 8.97 | 9.25 | 56.33 | -8.80 | 65.13* |
| 560.4 | 17.93 | 7.25 | 64.17 | 37.47 | 26.70* |
| 560.4 | 26.90 | 6.50 | 67.93 | 57.22 | 10.71 |

[1]LSD (0.05) = 21.86
*Synergistic, i.e. (obs.-exp.) > LSD

EXAMPLE 4

Evaluation Of The Herbicidal Activity Of A Combination Of Glyphosate And The R Isomer Of An Imidazolinone Compound In this evaluation pitted morningglory (*Ipomoea lacunosa*) and purple nutsedge (*Cyperus rotundus*) plants are grown in a 1:1 mixture of fine sandy loam soil and masonry sand to the 5–7 leaf stage for the pitted morningglory plants and the 10–15 leaf stage for the purple nutsedge plants. Said plants are then sprayed with an aqueous solution of test compound using a $CO_2$-pressurized spray chamber at a volume of 15 gallons/acre. Each treatment is replicated 4 times. After spraying, the plants are placed on greenhouse benches and cared for in a manner commensurate with conventional greenhouse practice. At regular intervals, plants are visually examined and % weed control as compared to the untreated check is recorded. The data are analyzed using standard statistical techniques to determine the least significant difference (LDS) or standard deviation. The Colby method is used to determine if the test combination demonstrates a synergistic interaction.

Test compounds

Glyphosate, isopropylamonnium salt (ROUNDUP ® ULTRA)[1]
Compound A = R isomer of imazapyr[2]
Compound B = R isomer of imazapic[2]
Compound C = R isomer of imazamox[2]
Compound D = R isomer of imazethapyr[2]

[1]Manufactured by Monsanto
[2]Formulated as an aqueous concentrate according to US 4,816,060

TABLE VIII

Evaluation of Control of Pitted Morningglory At 5 Weeks After Treatment

| Glyphosate | Imidazolinone | | % Weed Control | | |
|---|---|---|---|---|---|
| (g/ha) | Cmpd | (g/ha) | Observed | Expected | (Obs.-Exp.)[1] |
| 0 | | 0 | 0 | — | |
| 0 | A | 5.6 | 47.50 | — | |
| 0 | B | 9.0 | 22.50 | — | |
| 0 | C | 12.3 | 22.50 | — | |
| 0 | D | 23.5 | 22.50 | — | |
| 560 | | 0 | 3.75 | — | |
| 560 | A | 5.6 | 71.25 | 49.50 | 21.75* |
| 560 | B | 9.0 | 67.50 | 25.50 | 42.00* |
| 560 | C | 12.3 | 75.00 | 25.38 | 49.63* |
| 560 | D | 23.5 | 71.25 | 25.50 | 45.75* |

[1]LSD = 12.6
*Synergistic, i.e. (obs.-exp.) > LSD

TABLE IX

Evaluation of Control of Purple Nutsedge At 4 Weeks After Treatment

| Glyphosate | Imidazolinone | | % Weed Control | | |
|---|---|---|---|---|---|
| (g/ha) | Cmpd | (g/ha) | Observed | Expected | (Obs.-Exp.)[1] |
| 0 | | 0 | 0 | — | |
| 0 | A | 5.6 | 0 | | |
| 0 | B | 9.0 | 0 | | |
| 0 | C | 12.3 | 0 | | |
| 0 | D | 23.5 | 0 | | |
| 560 | | 0 | 15.00 | | |
| 560 | A | 5.6 | 38.33 | 15.00 | 23.33* |
| 560 | B | 9.0 | 40.00 | 15.00 | 25.00* |

TABLE IX-continued

Evaluation of Control of Purple Nutsedge At 4 Weeks After Treatment

| Glyphosate | Imidazolinone | | % Weed Control | | |
|---|---|---|---|---|---|
| (g/ha) | Cmpd | (g/ha) | Observed | Expected | (Obs.-Exp.)[1] |
| 560 | C | 12.3 | 38.33 | 15.00 | 23.33* |
| 560 | D | 23.5 | 60.00 | 15.00 | 45.00* |

[1]LSD = 9.7
*Synergistic, i.e. (obs.-exp.) > LSD

What is claimed is:

1. A method for the synergistic control of undesirable Ipomoea, Cyperus, Sida and Euphorbia plants which comprises applying to the locus of said plants or to the foliage or stems of said plants a synergistically effective amount of a combination of glyphosate and an imidazolinone compound selected from the group consisting of imazethapyr; imazaquin; imazapic; imazamox; imazapyr; and mixtures thereof.

2. The method according to claim 1 wherein said plants are Ipomoea or Cyperus.

3. The method according to claim 1 wherein the imidazolinone compound is imazethapyr.

4. The method according to claim 1 wherein the midazolinone compound is imazapic.

5. The method according to claim 1 wherein the imidazolinone compound is imazamox.

6. The method according to claim 2 wherein said plant is Ipomoea.

7. The method according to claim 1 wherein the glyphosate and imidazolinone compound are present at a wt/wt ratio of about 3:1 to 65:1.

8. The method according to claim 3 wherein the glyphosate and imazethapyr are present at a wt/wt ratio of about 8:1 to 12:1.

9. The method according to claim 4 wherein the glyphosate and imazapic are present at a wt/wt ratio of 15:1 to 65:1.

10. The method according to claim 5 wherein the glyphosate and imazamox are present at a wt/wt ratio of 20:1 to 65:1.

11. The method according to claim 1 wherein the synergistically effective amount is about 200 g/ha–1200 g/ha of glyphosate and about 8.0 g/ha–150 g/ha of an imidazolinone compound.

12. The method according to claim 3 wherein the synergistically effective amount is about 400 g/ha–800 g/ha of glyphosate and about 55 g/ha–100 g/ha of imazethapyr.

13. The method according to claim 12 wherein the synergistically effective amount is about 480 g/ha–720 g/ha of glyphosate and about 60 g/ha–80 g/ha of imazethapyr.

14. The method according to claim 3 wherein the compound is the R isomer of imazethapyr.

15. The method according to claim 4 wherein the compound is the R isomer of imazapic.

16. The method to claim 5 wherein the compound is the R isomer of imazamox.

* * * * *